(12) United States Patent
Choi

(10) Patent No.: US 11,819,366 B2
(45) Date of Patent: Nov. 21, 2023

(54) MEDICAL DEVICE CONTROL APPARATUS USING A HANDPIECE GESTURE AND SWITCH STATUS, AND METHOD FOR CONTROLLING THEREOF

(71) Applicants: Staronic Co., LTD, Seoul (KR); Jongwoon Choi, Seoul (KR)

(72) Inventor: Jongwoon Choi, Seoul (KR)

(73) Assignees: Staronic Co., LTD., Seoul (KR); Jongwoon Choi, Seoul (KR)

( * ) Notice: Subject to any disclaimer, the term of this patent is extended or adjusted under 35 U.S.C. 154(b) by 254 days.

(21) Appl. No.: 17/405,069

(22) Filed: Aug. 18, 2021

(65) Prior Publication Data
US 2022/0401176 A1 Dec. 22, 2022

(30) Foreign Application Priority Data
Jun. 18, 2021 (KR) .................. 10-2021-0079113

(51) Int. Cl.
*A61B 17/00* (2006.01)
*A61B 90/00* (2016.01)

(52) U.S. Cl.
CPC .............. *A61B 90/08* (2016.02); *A61B 17/00* (2013.01); *A61B 2017/00119* (2013.01); *A61B 2017/00207* (2013.01)

(58) Field of Classification Search
CPC ................................ A61B 17/00; A61B 90/18
USPC ............................................................ 606/1
See application file for complete search history.

(56) References Cited

U.S. PATENT DOCUMENTS 8,652,148 B2 * 2/2014 Zuhars ................ A61F 2/30756
606/86 R

* cited by examiner

*Primary Examiner* — Nadia A Mahmood (57) ABSTRACT

Provided are a medical device control apparatus using a handpiece motion and a control method using the same. The medical device control apparatus using the handpiece motion comprises a handpiece which is connected with a medical device body to perform a procedure; a gesture detector which is provided in the handpiece and detects the motion of the handpiece to recognize the gesture of the handpiece; an alarm unit which alarms that a mode of the medical device body is changed from a first state to a second state or parameter values are controlled according to the gesture of the handpiece; control switch which is provided in the handpiece to change the mode of the medical device body or control the parameter values output by the medical device body; and a connection cable which connects the medical device body and the handpiece.

10 Claims, 8 Drawing Sheets

MEDICAL DEVICE CONTROL APPARATUS USING A HANDPIECE GESTURE AND SWITCH STATUS, AND METHOD FOR CONTROLLING THEREOF

CROSS-REFERENCE TO RELATED APPLICATION

This application claims under 35 U.S.C. § 119(a) the benefit of Korean Patent Application No. 10-2021-0079113 filed on Jun. 18, 2021, the entire contents of which are incorporated herein by reference.

BACKGROUND

(a) Technical Field

The present invention relates to a medical device control apparatus using a handpiece motion and a control method thereof and more particularly, to an apparatus and a method for facilitating the use of a medical device by detecting a gesture or motion of a handpiece used with the medical device to improve the use convenience of the medical device including the handpiece.

(b) Background Art

Generally, a medical device consists of a handpiece performing a procedure and a medical device body responsible for energy generation and control. Medical devices, including handpieces, not only have a variety of functions for treatment, but also have stop and ready states to ensure the safety of an operator and a subject. The stop state means a forced state that prevents energy from being emitted through an operation of a footrest switch or a switch attached to the handpiece, and the ready state means a state in which the energy may be emitted by the operation of the footrest switch or the handpiece switch. The operator may adjust parameters of the medical device according to a procedure purpose before the procedure, and perform the procedure in the ready state. The procedure parameters can be changed only in the stop state through an operation plate attached to the medical device body, so that whenever the parameters are to be changed, the ready state and the stop state need to be cyclically changed. Therefore, the operator not only performs the procedure using a handpiece, but also operates the medical device body during the procedure depending on the need to change the parameters and change a mode of use. Alternately, the operator operates the medical device body with the help of a procedure assistant.

Such an operator performs the procedure while changing frequently the parameters during the procedure to obtain an optimal procedure result. To change the procedure parameters, there is inconvenience to adjust the medical device body while changing the hand holding the handpiece to the other hand. In addition, to perform a delicate procedure, it acts as an important factor to obtain the optimal procedure result to make an operation area of the operator as small as possible.

That is, when performing the procedure using the medical device with a conventional handpiece, the action of changing the parameters of the medical device or converting the medical device state to the ready or stop state is innumerably repeated. In order to perform such an operation, it is necessary to operate the switch by accessing a graphic user interface (GUI) attached to the medical device body or operate the medical device with the help of the assistant by enlarging the operation area of the operator. This causes a result in which the operator does not focus on the treatment and there is a problem to additionally receive the assistant's help.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention has been made in an effort to solve the problems and other problems. An object of the present invention is to provide a medical device control apparatus using a handpiece motion and a control method thereof.

According to an aspect of the present invention to solve the problem, there is provided a medical device control apparatus using a handpiece motion including: a handpiece which is connected with a medical device body to perform a procedure; a gesture detector which is provided in the handpiece and detects the motion of the handpiece to recognize the gesture of the handpiece; an alarm unit which alarms that a mode of the medical device body is changed from a first state to a second state or parameter values are controlled according to the gesture of the handpiece; control switch which is provided in the handpiece to change the mode of the medical device body or control the parameter values output by the medical device body; and a connection cable which connects the medical device body and the handpiece.

The change of the mode or the control of the parameter value may be able to be performed when the handpiece is detected as a first gesture or a second gesture, and the first gesture may be a state where the handpiece is located in a first angle range based on the gravity direction and the second gesture may be a state where the handpiece is located in a second angle range different from the first angle range based on the gravity direction.

The gesture detector may detect once or more impacts from the outside to change a mode or control an output intensity of the parameter.

According to another aspect of the present invention, there is provided a medical device control method using a motion of a handpiece connected with a medical device body including detecting a motion of the handpiece to determine whether the motion is a first gesture or a second gesture; alarming that the handpiece changes a mode to a first state or a second state or change a parameter value in the first gesture or the second gesture; and operating a control switch provided in the handpiece to change the mode of the medical device body or control the parameter value.

The first state may be a stop state of the medical device body and the second state may be a ready state of the medical device body.

The first gesture may be located in a predetermined first angle range based on the gravity direction of the handpiece and the second gesture may be located in a second angle range different from the first angle range based on the gravity direction of the handpiece.

The first gesture may be a clockwise rotation of the handpiece and the second gesture may be a counterclockwise rotation of the handpiece.

The first gesture and the second gesture may be moving in a predetermined direction as a movement of one or more direction conversions of the handpiece and the first gesture and the second gesture may have different movement directions or movement orders of the handpiece.

The change of the mode or the control of the parameter value may be performed by detecting a vibration generated by once or more impacts applied to the handpiece.

The first gesture or the second gesture which is different from each other may be taken while the control switch is operated in the stop state of the handpiece to control the parameter value.

The effects of the medical device control apparatus using the handpiece motion and the control method thereof according to the present invention will be described as follows.

According to at least one of the embodiments of the present invention, there is an advantage of controlling a medical device with a simple operation of an operator when controlling a medical device by using a technique of recognizing the motion (gesture) and the posture of the handpiece.

According to at least one of the embodiments of the present invention, since a space where the operator moves during the procedure is minimized, a procedure of using the medical device is comfortable. Therefore, the operator can more focus on the procedure.

The additional scope of the applicability of the present invention will become apparent from the following detailed description. However, since various modifications and changes within the spirit and scope of the present invention can be clearly understood to those skilled in the art, specific embodiments, such as preferred embodiments of the present invention, should be understood as just as illustrative purposes.

DETAILED DESCRIPTION

Hereinafter, embodiments disclosed in the present disclosure will be described in detail with reference to the accompanying drawings and the same or similar components are denoted by the same reference numerals regardless of a sign of the drawing, and duplicated description thereof will be omitted. Further, in describing the embodiment of the present disclosure, a detailed description of related known technologies will be omitted if it is determined that the detailed description makes the gist of the embodiment disclosed in the present disclosure unclear. Further, it is to be understood that the accompanying drawings are just used for easily understanding the embodiments disclosed in the present disclosure and a technical spirit disclosed in the present disclosure is not limited by the accompanying drawings and all changes, equivalents, or substitutes included in the spirit and the technical scope of the present invention are included.

In an embodiment of the present invention, a medical device control apparatus which is connected with a medical device body to control the medical device body and a medical device control method using the same. As an example, the medical device may be a device for performing the treatment by irradiating a laser and the handpiece means a part of performing a procedure of a patient while being held by the operator as a part where the laser is exposed to the outside.

Figure 1:
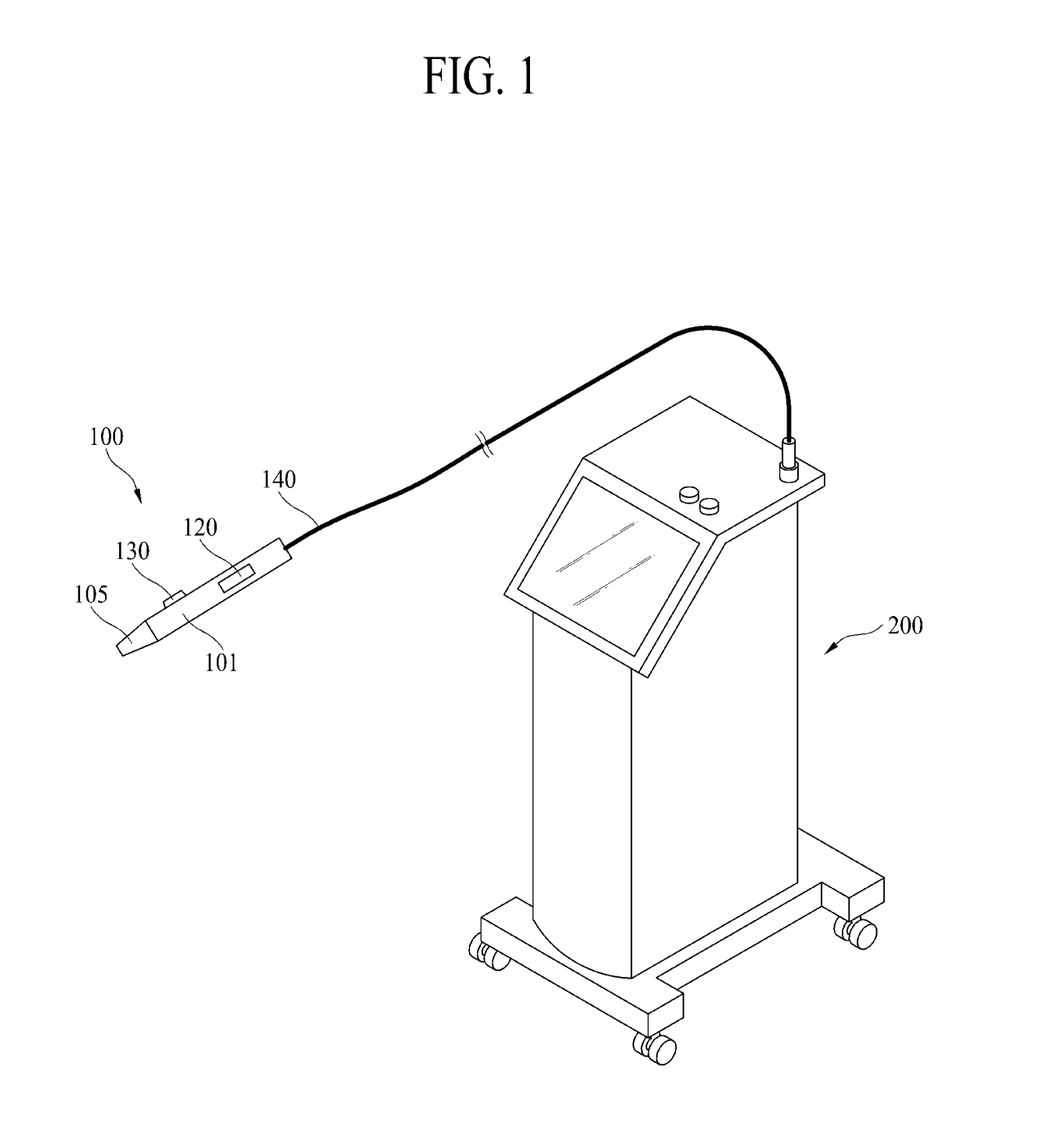
FIG. 1 is a configuration diagram of a medical device control apparatus provided in a medical device body according to an embodiment of the present invention.
Figure 2A:
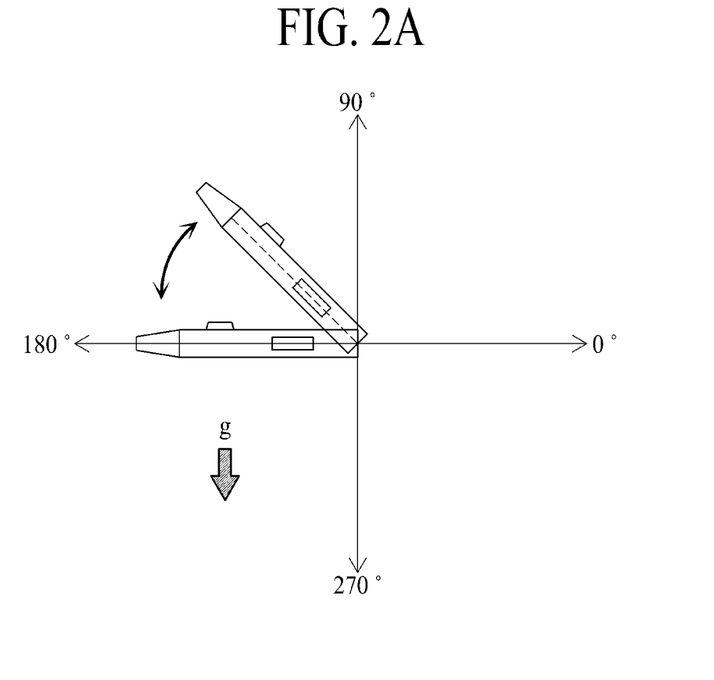
FIGS. 2A and 2B are operational diagrams for converting a medical device to a stop or ready state according to an embodiment of the present invention.
Figure 2B:
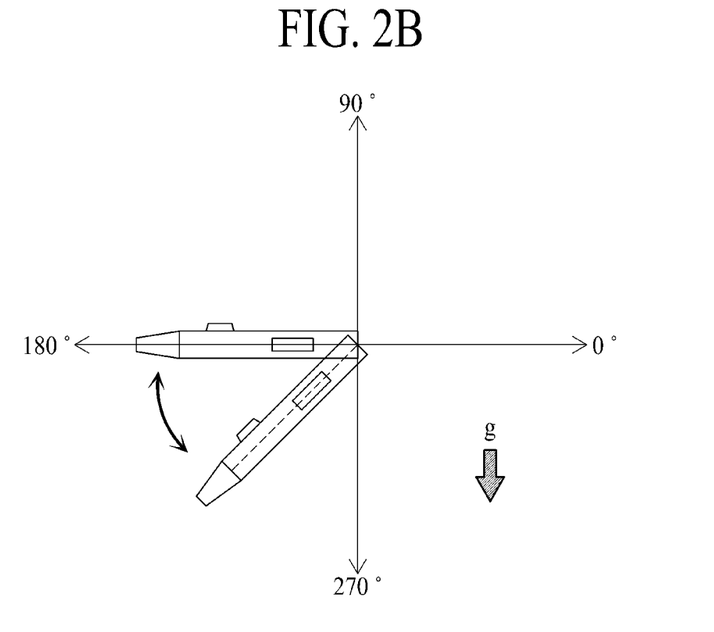
Figure 3A:
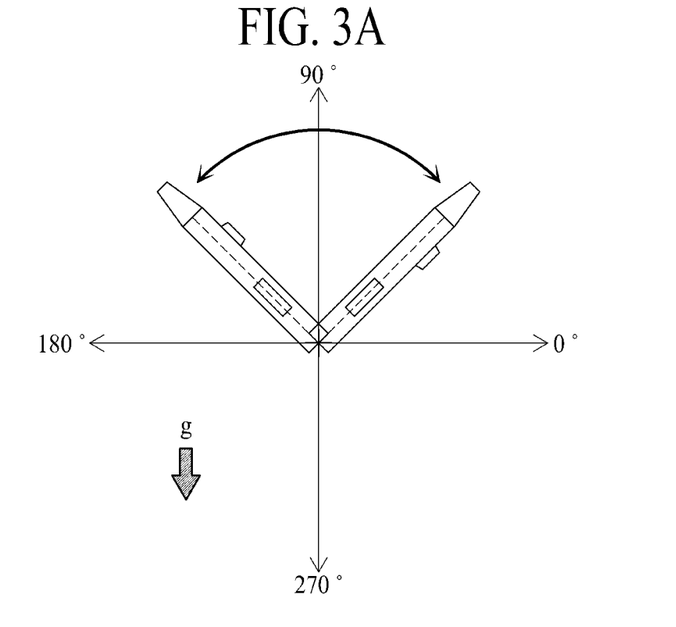
FIGS. 3A and 3B are operational diagrams for increasing or decreasing parameter values of the medical device according to the embodiment of the present invention.
Figure 3B:
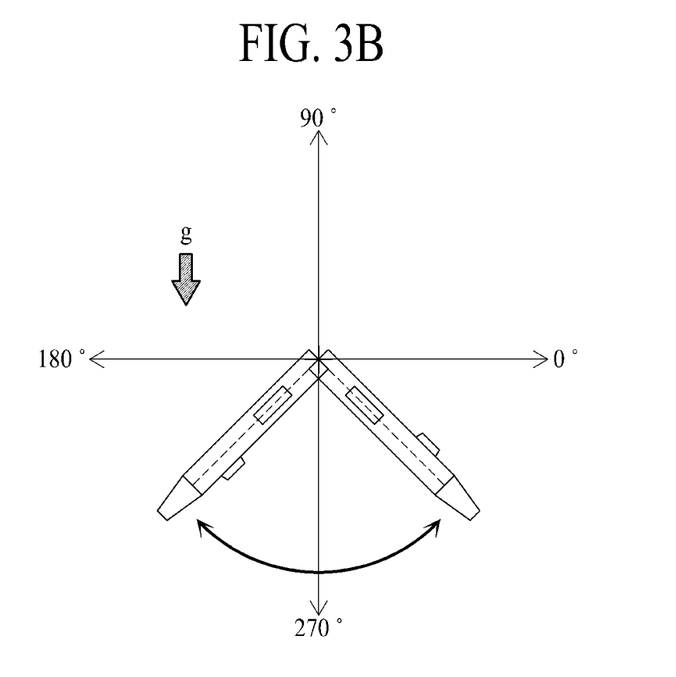

FIG. 1 is a configuration diagram of a medical device control apparatus 100 provided in a medical device body 200 according to an embodiment of the present invention, FIGS. 2A and 2B are operational diagrams for converting a medical device to a stop or ready state according to an embodiment of the present invention, and FIGS. 3A and 3B are operational diagrams for increasing or decreasing parameter values of the medical device according to the embodiment of the present invention.

Figure 13:
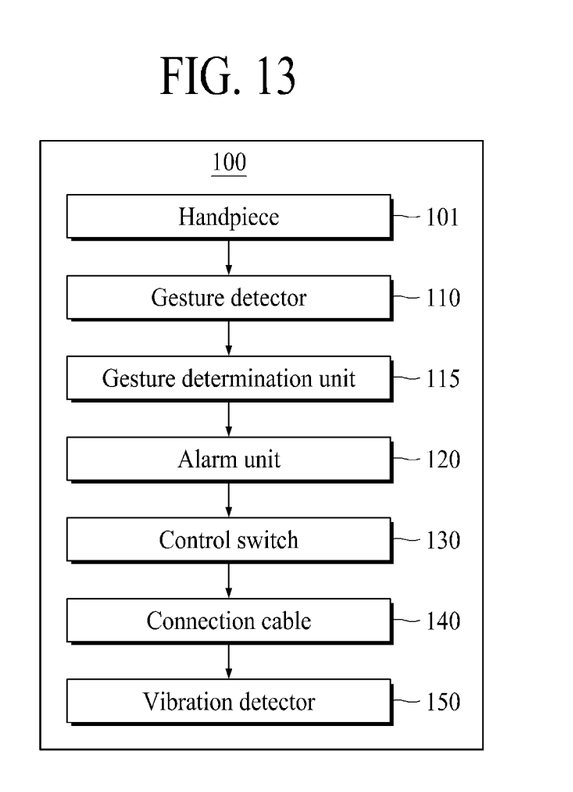
FIG. 13 is a block diagram of a handpiece according to the embodiment of the present invention.

Hereinafter, the present invention will be described with reference to FIGS. 1 to 3B. FIG. 13 is a block diagram of a handpiece according to an embodiment of the present invention. Referring to FIGS. 1 to 3B together with FIG. 13, a medical device control apparatus 100 according to an embodiment of the present invention includes a handpiece 101 which is connected with a medical device body 200 to perform a procedure, a gesture detector 110 which is provided in the handpiece 101 and detects the motion of the handpiece 101 to recognize the gesture of the handpiece 101, an alarm unit 120 which alarms that a mode of the medical device body 200 is changed from a first state to a second state or parameter values may be controlled according to the gesture of the handpiece 101, a control switch 130 which is provided in the handpiece 101 to change the mode of the medical device body 200 or control the parameter values output by the medical device body 200, and a connection cable 140 which connects the medical device body 200 and the handpiece 101. The alarm unit may be a haptic means such as a buzzer and a vibration generator.

The gesture detector 110 may measure not only a gravity acceleration direction but also a three-dimensional azimuth angle based on the gravity acceleration direction by using a gravity acceleration measuring detector such as a three-axial accelerometer. The posture of the handpiece 101 may be divided at 360° for convenience using the three-axial measurement value. That is, a right direction of a surface perpendicular to a gravity acceleration g direction as a vertical direction may be set to 0° and an angle size may be set in a counterclockwise direction. In order to activate the medical device, the control switch 130 is used as a method of inputting the determination of the operator as well as activating the medical device in an embodiment of the present invention. That is, the medical device may also be converted from the stop state to the ready state and the conversion from a current state to another state may also be determined. In an embodiment of the present invention, the stop state means a forced state in which the energy is not emitted despite the operation of the medical device body 200 or the handpiece 101 until being converted to the ready state, and the ready state means a state in which the energy may be emitted by the operation of the medical device body 200 or the handpiece 101.

In an embodiment of the present invention, the gesture detector 110 detects a posture, a moving direction, a moving speed, a moving acceleration, a rotational direction, refraction direction and refraction angle during moving, impact amount and impact number, etc. of the handpiece 101. The gesture detector 110 detects various movements, rotations, accelerations, impacts, etc. of the handpiece 101 to configure various gestures and may configure a specific state in a specific gesture or control an output intensity of the parameter. The first gesture and the second gesture described in the embodiment of the present invention mean states which may be introduced to different states, and the first gesture and the second gesture may also be configured to increase and decrease the parameter values other than the state conversion. For example, the first gesture may be configured to increase the value of the parameter and the second gesture may be configured to decrease the value of the parameter. On the contrary, even if the value of the parameter is increased or decreased by the first gesture and the second gesture to be described below, the state may be configured to be converted to the stop state or the ready state. That is, the first gesture and the second gesture of the present invention may be configured to convert the state or increase or decrease the parameter value. Further, in an embodiment of the present invention, a plurality of pairs of first gestures and second gestures are disclosed, and these pairs of first gestures and second gestures may be used alone or also used in combination with each other. For example, for the state conversion, the first gesture and the second gesture illustrated in FIGS. 5A and 5B may also be used to increase or decrease the parameter values while using the first gesture and the second gesture illustrated in FIGS. 4A and 4B. Since the operator may be confused by combining the plurality of pairs, it is preferable to use combinations of suitable pairs of first and second gestures.

FIGS. 2A and 2B illustrate a method of converting a usage mode of the medical device according to an embodiment of the present invention to a stop state or a ready state. Referring to FIGS. 2A and 2B, when the handpiece 101 is located in the range of any angle, for example, 45° to 135° which is an opposite direction to the gravity acceleration, the user may recognize the state of the medical device to be changed through conversion of a sound or operation screen. At this time, when the user presses the control switch 130, the state is recognized as a stop state.

Further, as illustrated in FIG. 2B, when the handpiece 101 is located in the range of any angle, for example, 225° to 315° based on a direction to the gravity acceleration, the user may recognize the state to be changed through conversion of a sound or operation screen. At this time, when the control switch 130 is pressed, the state is converted to the ready state. When the angle range in FIG. 2A is referred to as the first gesture and the angle range in FIG. 2B is referred to as the second gesture, in the first state, the medical device body 200 is converted to the stop state and the medical device body 200 may be converted to the ready state in the second gesture. However, in contrast, the medical device body 200 is converted to the ready state in the first gesture and the medical device body 200 may be converted to the stop state in the second gesture. At this time, in the case of the first gesture, the parameter value may be set to be increased and in the case of second gesture, the parameter value may also be set to be decreased.

Figure 11:
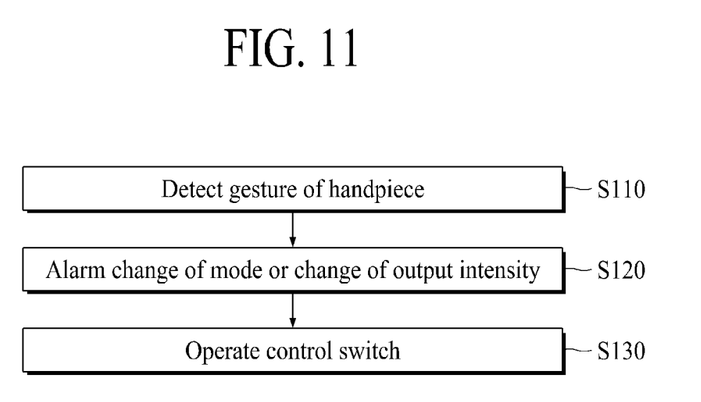
FIG. 11 is a flowchart of a control method of a medical device according to an embodiment of the present invention.

On the other hand, in an embodiment of the present invention, a control method for controlling a medical device which is connected to the medical device body 200 to control the medical device body 200, and FIG. 11 illustrates a flowchart of a control method of a medical device according to an embodiment of the present invention. Referring to FIG. 11, the control method includes detecting a motion of the handpiece 101 to determine whether the motion is a first gesture or a second gesture (S110), alarming that the handpiece 101 may change a mode to a first state or a second state or change a parameter value in the first gesture or the second gesture (S120), and operating a control switch provided in the handpiece 101 (S130) to change the mode of the medical device body 200 or control the parameter value. Whether the motion of the handpiece 101 is the first gesture or the second gesture is performed in a gesture determination unit 115.

The state of the medical device may vary depending on whether the handpiece 101 is the first gesture or the second gesture. That is, the first state may mean the stop state of the medical device body 200 and the second state may mean the ready state of the medical device body 200, and the reverse is possible. As illustrated in FIGS. 2A and 2B and FIGS. 3A and 3B, the first gesture may means being located in a predetermined first angle range based on the gravity direction of the handpiece 101 and the second gesture may mean being located in a second angle range different from the first angle range based on the gravity direction of the handpiece 101.

FIGS. 3A and 3B illustrate a method of increasing or decreasing the parameter value used in the medical device according to an embodiment of the present invention. In an embodiment of the present invention, when the medical device is a laser therapy device, the parameter may be the strength of the laser. Referring to FIGS. 3A and 3B, when the handpiece is introduced to an area inclined upward at any angle as illustrated in FIG. 3A based on a surface perpendicular to the gravity acceleration direction, the user may recognize through the conversion of the signal or operation screen that the state can be changed. At this time, the parameter value may be increased by pressing the control switch 130. As illustrated in FIG. 3B, when the handpiece 101 is located in an area inclined downward, the user may recognize through the conversion of the signal or operation screen that the state can be changed. At this time, the parameter value may be decreased by pressing the control switch 130. When the gesture of the handpiece 101 in FIG. 3A is referred to as the first gesture and the gesture of the handpiece 101 in FIG. 3B is referred to as the second gesture, in the first gesture, the parameter value may be set to be increased, and in the second gesture, the parameter value may be set to be decreased, and the reverse can be applied.

As such, in an embodiment of the present invention, the change of the mode or the change of the parameter value can be performed when the handpiece 101 is detected as the first gesture or the second gesture. The first gesture may be a case where the handpiece 101 is located in a first angle range based on the gravity direction and the second gesture may be a case where the handpiece 101 is located in a second angle range different from the first angle range based on the gravity direction. The first angle range and the second angle range may be set to face opposite directions for clear division, but are not necessarily limited thereto, and may be set even if being located neighboring quadrants based on a boundary between the quadrants based on 4 quadrants.

Figure 4A:
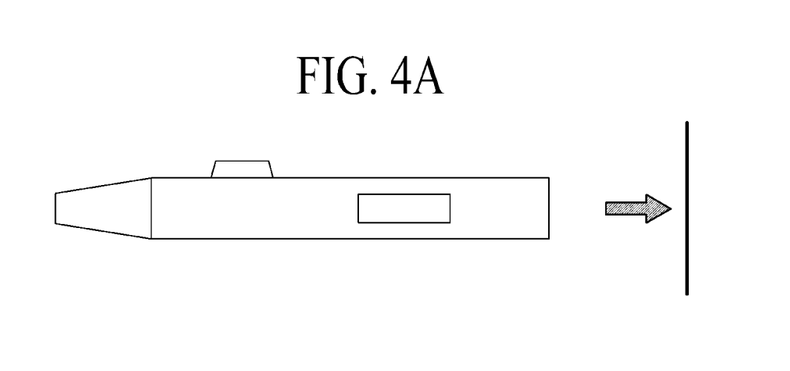
FIGS. 4A and 4B are operational diagrams of accelerating and then stopping a handpiece in an axial direction according to the embodiment of the present invention.
Figure 4B:
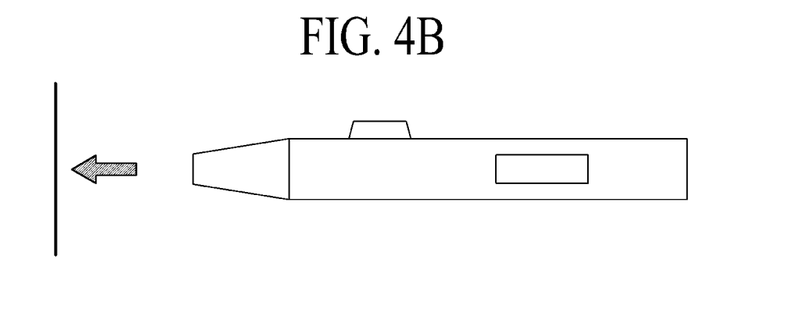
Figure 5A:
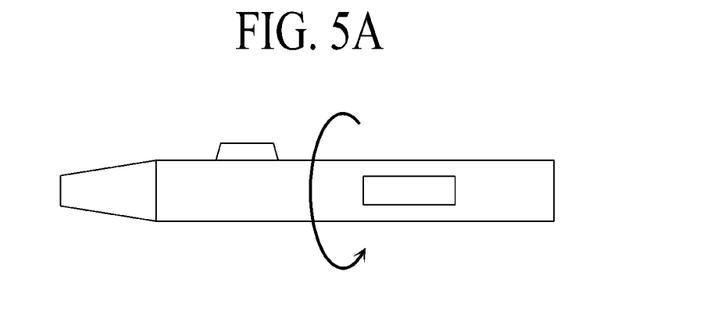
FIGS. 5A and 5B are operational diagrams of rotating a wrist holding the handpiece according to the embodiment of the present invention.
Figure 5B:
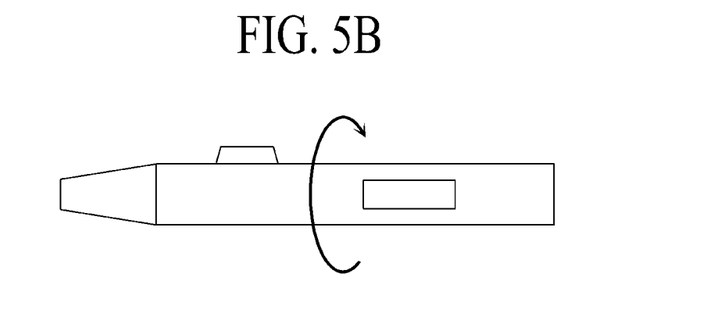
Figure 6A:
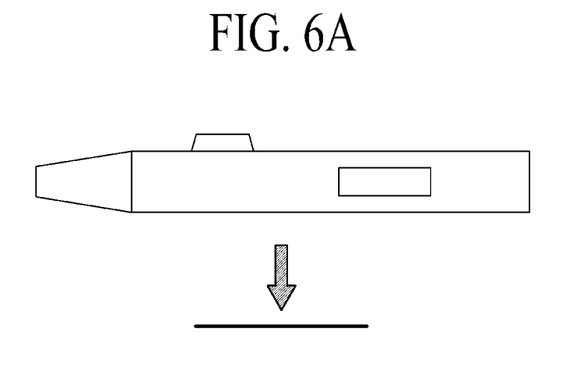
FIGS. 6A and 6B are operational diagrams of accelerating and then stopping a handpiece in a vertical direction according to the embodiment of the present invention.
Figure 6B:
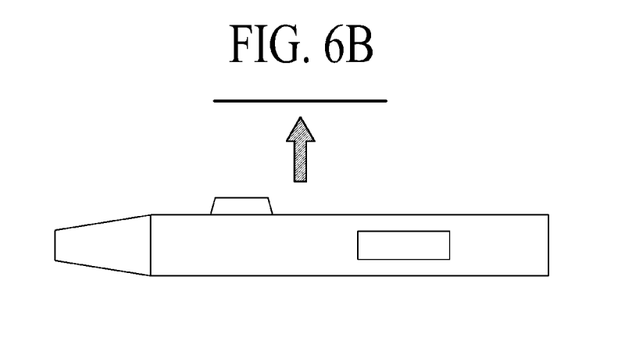

FIGS. 4A and 4B are operational diagrams of accelerating and then stopping the handpiece 101 in an axial direction according to the embodiment of the present invention, FIGS. 5A and 5B are operational diagrams of rotating the wrist holding the handpiece 101 according to the embodiment of the present invention, and FIGS. 6A and 6B are operational diagrams of accelerating and then stopping the handpiece 101 in a vertical direction according to the embodiment of the present invention.

First, referring to FIGS. 4A and 4B, FIGS. 4A and 4B illustrate a method of increasing or decreasing the parameter value of the medical device, and the first gesture may be an operation of accelerating and then stopping the handpiece 101 in a first direction and the second gesture may be an operation of accelerating and then stopping the handpiece 101 in a second direction different from the first direction. As illustrated in FIG. 4A, an operation of accelerating in a rear direction and then suddenly stopping the handpiece 101 while the control switch 130 is pressed is recognized as the operation of decreasing the parameter value. On the contrary, as illustrated in FIG. 4B, an operation of accelerating forward and then suddenly stopping the handpiece 101 may be recognized as the operation of increasing the parameter value. When the state of FIG. 4A is referred to as the first gesture and the state of FIG. 4B is referred to as the second gesture, the parameter value is set to be decreased in the first gesture and the parameter value is set to be increased in the second gesture. Of course, on the contrary, in the first gesture, the parameter value may be set to be increased and in the second gesture, the parameter value may also be set to be decreased. At this time, the acceleration of the handpiece 101 can be detected.

As illustrated in FIGS. 5A and 5B, the first gesture may be a counterclockwise rotation of the handpiece 101 and the second gesture may be a clockwise rotation of the handpiece 101. Referring to FIG. 5, FIGS. 5A and 5B illustrate a method of increasing or decreasing the parameter value of the medical device, and as illustrated in FIG. 5A, when the handpiece 101 rotates counterclockwise based on the wrist holding the handpiece 101 and then stops while the control switch 130 is pressed, the parameter value is increased. Further, as illustrated in FIG. 5B, when the handpiece 101 rotates clockwise based on the wrist holding the handpiece 101 and then stops while the control switch 130 is pressed, the parameter value is decreased. Of course, in the first gesture, the parameter value may be decreased, and in the second gesture, the parameter value can be increased.

Referring to FIGS. 6A and 6B, FIGS. 6A and 6B illustrate a method of increasing or decreasing the parameter value of the medical device, and as illustrated in FIG. 6A, when the handpiece 101 accelerates in a first direction and then stops while the control switch 130 is pressed, the parameter value is increased. In addition, as illustrated in FIG. 6B, when the handpiece 101 accelerates in a second direction different from the first direction and then stops while the control switch 130 is pressed, the parameter value is decreased. When the state of FIG. 6A is referred to as the first gesture and the state of FIG. 6B is referred to as the second gesture, the parameter value is set to be increased in the first gesture and the parameter value is set to be decreased in the second gesture. Of course, on the contrary, in the first gesture, the parameter value may be set to be decreased and in the second gesture, the parameter value may also be set to be increased. At this time, the acceleration of the handpiece 101 can be detected. This is similar to FIGS. 4A and 4B.

Figure 7:
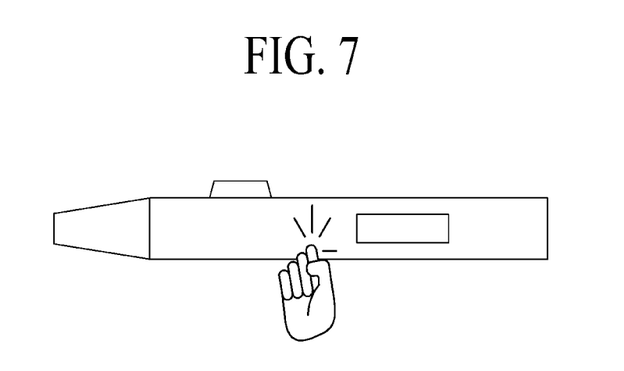
FIG. 7 is an operational diagram of lightly tapping the outside of the handpiece according to the embodiment of the present invention.

Meanwhile, in an embodiment of the present invention, there is provided a method of increasing or decreasing the parameter value of the medical device or a method of changing a stop state to a ready state by an operation of tapping the outside of the handpiece 101 once or more. FIG. 7 is an operational diagram of tapping the outside of the handpiece 101 once or twice according to the embodiment of the present invention. Referring to FIG. 7, the medical device is changed to the stop state or the ready state by an operation of lightly knocking the outside of the handpiece 101 with a nail tip or a finger once or twice while the control switch 130 is pressed. In addition, the operation may be applied to a parameter change. For example, at the time of once knocking, the parameter value may be increased, and at the time of twice knocking, the parameter value may be decreased. Of course, the reverse can be applied.

As such, in an embodiment of the present invention, the change of the mode or the control of the parameter value may be performed by detecting a vibration generated by once or more impacts applied to the handpiece 101. The vibration at this time is detected by a vibration detection unit 150 and the number of vibration times is counted, and the gesture determination unit 115 may determine the first gesture or the second gesture according to the number of vibration times.

Figure 12:
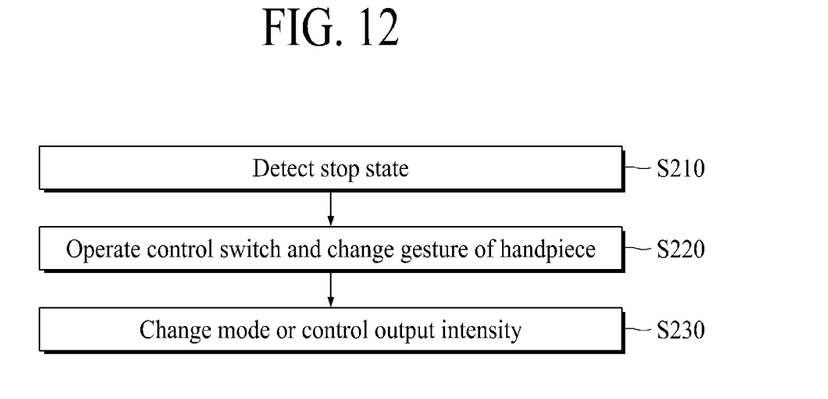
FIG. 12 is a flowchart of a control method of a medical device according to an embodiment of the present invention.

Furthermore, in an embodiment of the present invention, there is provided a method of increasing or decreasing the parameter value of the medical device or a method of changing the stop state to the ready state. For example, the first gesture or the second gesture is taken while the control switch 130 is operated to control an output intensity of the parameter. That is, the first gesture or the second gesture is taken while the control switch 130 is operated in the stop state of the handpiece 101 to control an output intensity of the parameter. FIG. 12 is a flowchart of a control method of a medical device according to the embodiment of the present invention, and first, the stop state of the medical device body 200 is detected (S210) to secure the safety, and then the gesture of the handpiece 101 is changed (S120) while the control switch 130 is operated to change the mode of the medical device or control the parameter value (S230). Step S210 corresponds to step S110 in FIG. 11 and step S220 corresponds to step S130 in FIG. 11.

Figure 8A:
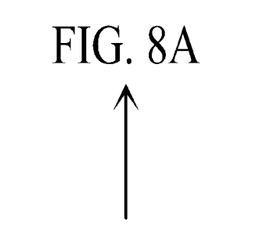
FIGS. 8A, 8B, 8C and 8D are operational diagrams of moving the handpiece in upper, lower, left, and right directions while holding the handpiece according to the embodiment of the present invention.
Figure 8B:
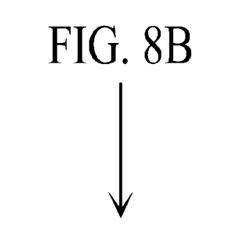
Figure 8C:
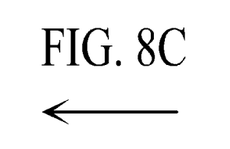
Figure 8D:
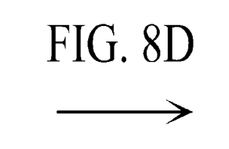
Figure 9A:
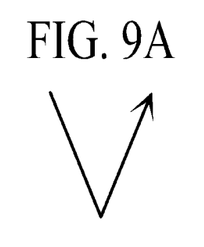
FIGS. 9A, 9B, 9C and 9D are operational diagrams of moving the handpiece in a V shape while holding the handpiece according to the embodiment of the present invention.
Figure 9B:
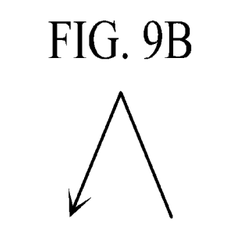
Figure 9C:
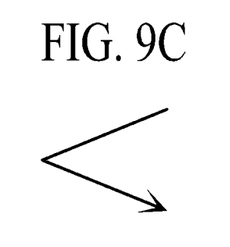
Figure 9D:
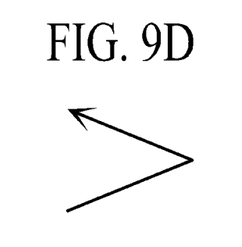
Figure 10A:
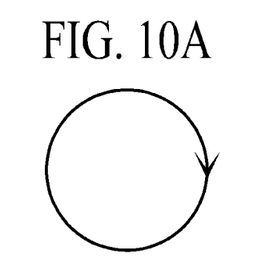
FIGS. 10A and 10B are operational diagrams of rotating the handpiece clockwise or counterclockwise while holding the handpiece according to the embodiment of the present invention.
Figure 10B:
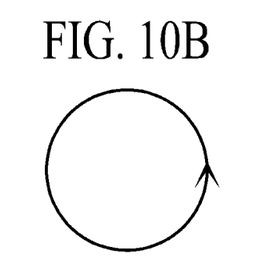

FIGS. 8A to 8D are operational diagrams of moving the handpiece 101 in upper, lower, left, and right directions while holding the handpiece 101 according to the embodiment of the present invention, FIGS. 9A to 9D are operational diagrams of moving the handpiece 101 in a V shape or a reverse V shape while holding the handpiece 101 according to the embodiment of the present invention, and FIGS. 10A and 10B are operational diagrams of rotating the handpiece 101 clockwise or counterclockwise while holding the handpiece 101 according to the embodiment of the present invention.

Referring to FIGS. 8A to 8D, when the medical device is in the stop state, while the control switch 130 is pressed, a direction facing a front end 105 of the handpiece 101 is shaken upward as illustrated in FIG. 8A to increase the parameter value and shaken downward as illustrated in FIG. 8B to decrease the parameter value. Unlike this, the shaking direction and the increase or decrease in the parameter may be applied reversely. Further, as illustrated in FIGS. 8C and 8D, the front end 105 of the handpiece 101 is shaken in a left or right direction to increase or decrease the parameter value.

As illustrated in FIGS. 9A to 9D, in an embodiment of the present invention, the first gesture and the second gesture may be moving in a predetermined direction as a movement of one or more direction conversions of the handpiece 101 and the first gesture and the second gesture may have different movement directions or movement orders of the handpiece 101. Referring to FIGS. 9A to 9D, when the medical device is in the stop state, while the control switch 130 is pressed, a direction facing the handpiece 101 is shaken in a V shape as illustrated in FIG. 9A to increase the parameter value and shaken in a reverse V shape as illustrated in FIG. 9B to decrease the parameter value. When such an operation is continuously performed, the parameter value may be continuously changed. In some cases, this may be applied in reverse. In addition, the parameter value may be set according to a V shape in which the handpiece 101 faces the left side as illustrated in FIG. 9C, or set according to a V shape in which the handpiece 101 faces the right side as illustrated in FIG. 9D.

In addition, referring to FIGS. 10A and 10B, when the medical device body 200 is in the stop state, as illustrated in FIG. 10A, when the facing direction of the handpiece 101 rotates clockwise while the control switch 130 is pressed, the parameter value may be set to be increased, and as illustrated in FIG. 10B, when the handpiece 101 rotates counterclockwise, the parameter value may be set to be decreased. When such an operation is continuously performed, the parameter value may be continuously changed. The rotation direction and the increase or decrease in the parameter may also be applied reversely.

The aforementioned detailed description should not be construed as restrictive in all aspects and should be exemplarily considered. The scope of the present invention should be determined by rational construing of the appended claims and all modifications within an equivalent scope of the present invention are included in the scope of the present invention.

What is claimed is:

1. A medical device control apparatus using a handpiece motion comprising:
    a handpiece which is connected with a medical device body to perform a procedure;
    a gesture detector which is provided in the handpiece and detects the motion of the handpiece to recognize the gesture of the handpiece;
    an alarm unit which alarms that a mode of the medical device body is changed from a first state to a second state or parameter values are controlled according to the gesture of the handpiece;
    a control switch which is provided in the handpiece to change the mode of the medical device body or control the parameter values output by the medical device body; and
    a connection cable which connects the medical device body and the handpiece,
    wherein the gesture detector configures various gestures of the handpiece based on a variety of movements, rotations, accelerations of the handpiece, or impacts on the handpiece; and,
    wherein the gesture detector configures one or more of the states within the configured gesture or controls an output intensity of the parameter according to the configured gesture.

2. The medical device control apparatus using the handpiece motion of claim 1, wherein the change of the mode or the control of the parameter value is able to be performed when the handpiece is detected as a first gesture or a second gesture, and
    the first gesture is a state where the handpiece is located in a first angle range based on the gravity direction and the second gesture is a state where the handpiece is located in a second angle range different from the first angle range based on the gravity direction.

3. The medical device control apparatus using the handpiece motion of claim 1, wherein the gesture detector detects once or more impacts from the outside to change a mode or control an output intensity of the parameter.

4. A medical device control method using a motion of a handpiece connected with a medical device body comprising:
    detecting a motion of the handpiece to determine whether the motion is a first gesture or a second gesture;
    alarming that the handpiece changes a mode to a first state or a second state or change a parameter value in the first gesture or the second gesture; and
    operating a control switch provided in the handpiece to change the mode of the medical device body or control the parameter value,
    wherein the gesture detector configures various gestures of the handpiece based on a variety of movements, rotations, accelerations of the handpiece, or impacts on the handpiece; and,
    wherein the gesture detector configures one or more of the states within the configured gesture or controls an output intensity of the parameter according to the configured gesture.

5. The medical device control method using the handpiece motion of claim 4,
    wherein the first gesture is located in a predetermined first angle range based on the gravity direction of the handpiece and the second gesture is located in a second angle range different from the first angle range based on the gravity direction of the handpiece.

6. The medical device control method using the handpiece motion of claim 4,
    wherein the first gesture is an operation of accelerating and then stopping the handpiece in a first direction and the second gesture is an operation of accelerating and then stopping the handpiece in a second direction different from the first direction.

7. The medical device control method using the handpiece motion of claim 4,
    wherein the first gesture is a clockwise rotation of the handpiece and the second gesture is a counterclockwise rotation of the handpiece.

8. The medical device control method using the handpiece motion of claim 4,
    wherein the first gesture and the second gesture are moving in a predetermined direction as a movement of one or more direction conversions of the handpiece and the first gesture and the second gesture have different movement directions or movement orders of the handpiece.

9. The medical device control method using the handpiece motion of claim 4, wherein the change of the mode or the control of the parameter value is performed by detecting a vibration generated by once or more impacts applied to the handpiece.

10. The medical device control method using the handpiece motion of claim 4, wherein the first gesture or the second gesture which is different from each other is taken while the control switch is operated in the stop state of the handpiece to control the parameter value.

* * * * *